(12) United States Patent
Suzuki et al.

(10) Patent No.: US 6,432,439 B1
(45) Date of Patent: *Aug. 13, 2002

(54) O/W EMULSION COMPOSITION

(75) Inventors: Hidekazu Suzuki; Satoshi Yamazaki; Yoshikazu Naito; Masanobu Takeuchi; Yoshiaki Saito, all of Chuo-Ku (JP)

(73) Assignee: Wakamoto Pharmaceutical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/541,682

(22) Filed: Apr. 3, 2000

(30) Foreign Application Priority Data

Oct. 1, 1997 (JP) ............................................... 9-283195

(51) Int. Cl.$^7$ ........................ A61K 31/56; A61K 31/57; A61K 9/107; A61F 2/00; A61F 13/00

(52) U.S. Cl. ........................ 424/427; 424/428; 514/169; 514/178; 514/179; 514/912; 514/914; 514/938; 514/939; 514/943

(58) Field of Search ................................ 424/400, 422, 424/427, 428, 450; 514/169, 178, 179, 912–915, 938–943

(56) References Cited

U.S. PATENT DOCUMENTS 5,744,155 A * 4/1998 Friedman
6,132,751 A * 10/2000 Suzuki

FOREIGN PATENT DOCUMENTS

| JP | 53-121920 | 10/1978 |
|----|-----------|---------|
| JP | 60-199833 | 9/1985 |
| JP | 62230726 | * 10/1987 |
| JP | 5-186333 | 7/1993 |
| JP | 9/255529 | 9/1997 |
| JP | WO99/16471 | 4/1999 |
| WO | WO 93/15736 | 8/1993 |
| WO | WO 96/40051 | 12/1996 |
| WO | WO-97/05882 | 2/1997 |

OTHER PUBLICATIONS

Joel L. Zatz, et al., J. Soc. Cosmet. Chem., No. 37, pp. 329 to 350, "Stabilization of Oil–in–Water Emulsions by Gums", Sep./Oct. 1986.

Kingo Uji, et al., J. Soc. Cosmet. Chem. Jpn., vol. 27, No. 3, pp. 206 to 215, "The Properties of Lecithin and Lecithin–Liposome Containing Emulsions, Emulsified with Crosslinked Acrylic Acid–Alkyl Acrylate Crosspolymer", 1993 (with partial English translation).

Rampurna P. Gullapalli, et al., International Journal of Pharmaceutics, vol. 140, pp. 97 to 109, "Effect of Methylcellulose on the Stability of Oil–In–Water Emulsions", 1996.

* cited by examiner

Primary Examiner—Gollamudi S. Kishore
(74) Attorney, Agent, or Firm—Oblon, Spivak, McClelland, Maier & Neustadt, P.C.

(57) ABSTRACT

An O/W emulsion composition comprising fluorometholone or clobetasone butyrate, a phospholipid, an oil, a nonionic water-soluble cellulose derivative, and water. The O/W composition has advantages that fluorometholone or clobetasone butyrate contained therein is highly bioavailable and that the solubility of fluorometholone or clobetasone butyrate and the concentration thereof present in the composition can be kept stable. Thus, this composition is usable for the treatment of various inflammatory diseases by the generalized or local administration thereof. It provides a drug which shows an anti-inflammatory activity equal or higher than that of commercially available eye drops comprising a suspension of such an active ingredient even when it is applied in a smaller dose than that of commercially available one and further provides a drug having excellent storability, which reduces apprehension of systemic side effects of fluorometholone or clobetasone butyrate when it is applied to the eyes.

18 Claims, No Drawings

O/W EMULSION COMPOSITION

TECHNICAL FIELD

The present invention relates to an O/W emulsion composition in which fluorometholone or clobetasone butyrate is highly soluble in body fluids such as blood and lachrymal fluid and having excellent property of keeping the solubility and concentration of fluorometholone or clobetasone butyrate contained in the composition.

BACKGROUND ART

Fluorometholone and clobetasone butyrate are synthetic adrenocortical hormones having a strong anti-inflammatory activity. Fluorometholone is effective in the treatment of the inflammatory diseases of outer ocular area and anterior segment of the eye, and clobetasone butyrate is effective in the treatment of the inflammatory diseases of eyes and also those of the skin. It is expected that these drugs are also effective in the treatment of the local and generalized inflammatory diseases other than those described above. However, because these drugs are hardly soluble in water, it is impossible to dispense these drugs in the form of ordinary aqueous preparations such as eye drops and parenteral injections. Therefore, in the ophthalmic field, fluorometholone and clobetasone butyrate have been each used in the form of an aqueous suspension which is prepared by finely pulverizing the crystals thereof and dispersing and suspending a suitable amount of the fine crystals in an aqueous liquid for eye drops. However, because these drugs are hardly soluble in water, the degree of dissolution of these drugs in the form of crystalline particles, contained in the aqueous suspension, into the lachrymal fluid is low and, accordingly, the bioavailability is extremely low.

It is known that the bioavailability of a hardly soluble drug generally depends on the solubility of the drug in water. For example, when such a hardly soluble drug is administered in the form of an oral solid preparation, the rate of release of the drug from the preparation thereof and dissolution of the drug are the rate-controlling step for the absorption of the drug (see "Iyakuhin no Bioavailability to Seibutsugaku-teki Dotosei Shiken"written by. Hiroyasu Ogata and Masayoshi Samejima and published by Yakugyo Jiho, inc.). In addition, when such a hardly soluble drug in the form of its suspension is applied to the eyes, transition of the drug into the eye tissue depends on the dissolution rate of the drug from the crystalline particles diluted with the lachrymal fluid [J. Pharm. Sci., 64 (6), 931–936 (1975)]. Namely, the bioavailability can be improved if the concentration of the administered, hardly soluble drug in the body fluids could be increased.

WO 97/05882 discloses that an O/W emulsion comprising fluorometholone or clobetasone butyrate as a drug, a phospholipid, a liquid paraffin and water improves the solubility of the drug in the lachrymal fluid to improve transfer of the drug into the eye tissue. However, this publication is silent on the influence of the additives on the nature of the composition to improve the solubility of fluorometholone or clobetasone butyrate in the lachrymal fluid, and also on the additives used for improving the solubility. This publication is also silent on the stability of the dissolution concentration of these drugs in the lachrymal fluid and of the concentration of these drugs in the composition during the storage. The inventors examined the storability of the emulsion preparations to find that both fluorometholone and clobetasone butyrate were crystallized during the storage and the ability of the composition to improve the solubility of these drugs in the lachrymal fluid were lowered.

As for the techniques of improving the stability of such a kind of emulsion, various emulsions comprising a water-soluble polymer were disclosed [see WO 93/15736, WO 96/40051, Japanese Patent Unexamined Published Application (hereinafter referred to as "J. P. KOKAI") No. Sho 53-121920, J. Soc. Cosmet. Chem., 37, 329–350 (1986), J. SCCJ, 27 (3), 206–215 (1993), and Int. J. Pharm., 140 (1), 97–109 (1996)]. However, these prior techniques are silent on the solubility of the drug in the body fluids and also on the improvement in the stability of the concentration of the drug contained in the composition (hereinafter referred to as "drug concentration"). J. P. KOKAI No. Hei 5-186333 discloses that an ophthalmic O/W emulsion composition comprising a drug, an oil, a phospholipid and an amphoteric surfactant is capable of keeping the average particle diameter and the drug concentration thereof during the storage.

DISCLOSURE OF THE INVENTION

The present invention has been developed for the purposes of improving the solubility of the conventional, hardly water-soluble drug in the body fluid and the stability of the improved solubility of the drugs in the body fluids. The object of the present invention is to provide a novel composition containing fluorometholone or clobetasone butyrate highly soluble in body fluids such as blood and lachrymal fluid and having excellent property of keeping the solubility of these drugs into body fluids and concentration of fluorometholone or clobetasone butyrate contained in the composition. After intensive investigations made for the purpose of attaining the above-described object, the inventors have found that an O/W emulsion composition containing fluorometholone or clobetasone butyrate, a phospholipid, an oil, a nonionic water-soluble cellulose derivative and water shows a high solubility of fluorometholone or clobetasone butyrate in the body fluids and such a high solubility thereof and the concentration of fluorometholone or clobetasone butyrate contained in the composition can be kept stable during the storage. The inventors have further found that when at least one member of the group consisting of chelating agents, polycarboxylic acid compounds and pharmaceutically acceptable salts thereof is incorporated into the emulsion composition, the solubility of fluorometholone or clobetasone butyrate in the body fluids and the concentration of fluorometholone or clobetasone butyrate contained in the composition can be kept stable for a far longer period of time. The present invention has been completed on the basis of these findings.

Namely, the present invention provides an O/W emulsion composition containing fluorometholone or clobetasone butyrate, a phospholipid, an oil, a non-ionic water-soluble cellulose derivative and water and, if necessary, at least one member of the group consisting of chelating agents, polycarboxylic acid compounds and pharmaceutically acceptable salts thereof. The present invention is characterized in that the solubility of fluorometholone and clobetasone butyrate in the body fluids is improved by incorporating the nonionic water-soluble cellulose derivative as an indispensable component. Other characteristic features of the present invention are that the solubility of fluorometholone and clobetasone butyrate in the body fluids is high and that the concentration of fluorometholone and clobetasone butyrate in the composition can be kept stable during the storage. By suitably changing the proportion of the constituents and amounts thereof, the O/W emulsion composition having a particularly high solubility of fluorometholone or clobetasone butyrate in the body fluids can be obtained, and the solubility and the concentration of fluorometholone or clobetasone butyrate contained in the composition can be kept stable for a longer period of time in the present invention. The O/W emulsion composition containing fluorometholone or clobetasone butyrate can be given to the patients by the systemic administration method or topical administration method in a suitable preparation form such as liquids for internal use, injections, ear drops, nasal drops, eye drops, aerosols or inhalations depending on the need. The O/W emulsion composition is usable for the treatment of diseases such as chronic hypoadrenocorticism, acute chronic hypoadrenocorticism, chronic articular rheumatism, ankylosing spondylitis, lupus erythematodes, systemic angitis, polymyositis, nephrosis and nephrotic syndrome, congestive heart failure, bronchial asthma, asthmatic bronchitis, allergy and intoxication caused by drugs and other chemical substances, severe infectious diseases, hemolytic anemia, leukemia, aplastic anemia, localized enteritis, tumorous colitis, fulminant hepatitis, chronic hepatitis, hepatic cirrhosis, sarcoidosis, diffuse interstitial pneumonia, post-invasion pulmonary edema, tuberculous meningitis, tuberculous pleurisy, tuberculous peritonitis, tuberculous pericarditis, encephalomyelitis, peripheral neuritis, spinal arachnoiditis, malignant lymphoma, adrenalectomy, organ and tissue transplantation, snake poison, insect poison, acute eczema, chronic eczema, contact dermatitis, autosensitization dermatitis, atopic dermatitis, neurodermatitis, dermatitis seborrhoica, hives, psoriasis and analogous diseases, anaphylactoid purpura, mucocutaneos ocular syndrome, Raynaud's disease, pemphigus group, herpes zoster, allergic angitis and analogous diseases, inflammatory diseases of intaocular, optic nerve, orbit and ocular muscle, inflammatory diseases of outer ocular area and anterior segment of the eye (when the application of eye drops is unsuitable or insufficient in the symptomatic therapy), acute and chronic otitis media, vasomotor rhinitis, allergic rhinitis, pollenosis, progressive gangrenous rhinitis, pharyngeal catarrh and pharyngeal enema, pharyngeal polyp and nodule, esophagitis and esophageal dilation operation (aftercare), otorhinolaryngologic operation (aftercare), intractable stomatitis and glossitis, acute and chronic (recurrent) sialadenitis, anaphylactic shock, retiochoroiditis, retinal vasculitis, optic neuritis, orbital inflammatory pseudotumor, orbital apex syndrome, opthalmoplegia, inflammatory diseases of outer ocular area and anterior segment of the eye such as blepharitis, conjunctivitis, keratitis, scleritis, episcleritis, iritis, iridocyclitis, uveitis and postoperative inflammations.

DESCRIPTION OF THE PREFERRED EMBODIMENTS

The detailed description will be made below on the present invention.

The nonionic, water-soluble cellulose derivatives contained in the O/W emulsion composition (hereinafter referred to as "emulsion") of the present invention are not particularly limited. They include, for example, methylcellulose, hydroxypropylmethylcellulose, hydroxypropylcellulose, hydroxyethylcellulose and hydroxyethylmethylcellulose. The degree of substitution and viscosity grade of the nonionic, water-soluble cellulose derivative are not particularly limited. The nonionic, water-soluble cellulose derivatives having any degree of substitution and any viscosity grade are usable in the present invention. At least one of the nonionic, water-soluble cellulose derivatives is incorporated into the emulsion of the present invention.

Among those nonionic, water-soluble cellulose derivatives, methylcellulose and hydroxypropylmethylcellulose are preferred because when either of them is used, a high concentration of fluorometholone (hereinafter referred to as "FLM") or clobetasone butyrate (hereinafter referred to as "CB") dissolved in the body fluids can be obtained, and the dissolution concentration thereof and also the concentration of FLM or CB contained in the composition (hereinafter referred to as "FLM concentration" or "CB concentration") can be kept stable for a longer period of time. Methylcellulose is the most preferred.

These nonionic, water-soluble cellulose derivatives are easily available on the market under the trade names of Metolose (registered trademark) SM-15, Metolose SM-25, Metolose SM-100, Metolose SM-400, Metolose SM-1500, Metolose SM-4000 and Metolose SM-8000 (methylcellulose; products of Shin-Etsu Chemical Co., Ltd.); TC-5E, TC-5MW, TC-5R, TC-5S, Metolose (registered trademark) 60SH-50 and Metolose 60SH-4000 (Hydroxypropylmethylcellulose 2910; Shin-Etsu Chemical Co., Ltd.); Metolose (registered trademark) 65SH-50, Metolose 65SH-400, Metolose 65SH-1500 and Metolose 65SH-4000 (Hydroxypropylmethylcellulose 2906; Shin-Etsu Chemical Co., Ltd.); SB-4, Metolose (registered trademark) 90SH-100, Metolose 90SH-400, Metolose 90SH-4000 and Metolose 90SH-30000F (Hydroxypropylmethylcellulose 2208; Shin-Etsu Chemical Co., Ltd.); FUJICHEMI HEC CF-H (hydroxyethylcellulose; Fuji Chemical Co., Ltd.); Tylose (registered trademark) H30OG4PHA (hydroxyethylcellulose; Clariant (Japan) K. K.); Shin-Etsu HPC (hydroxypropylcellulose; Shin-Etsu Chemical Co., Ltd.); and Tylopur (registered trademark) MH300G4 (hydroxyethylmethylcellulose; Clariant (Japan) K. K.).

The amount of the nonionic, water-soluble cellulose derivative used is usually 0.0005 to 5 w/v %, preferably 0.001 to 1 w/v %, more preferably 0.005 to 0.5 w/v %, and most preferably 0.025 to 0.5 w/v %. When the amount of the nonionic, water-soluble cellulose derivative used is 0.0005 w/v % or higher, the stability of the dissolution concentration of FLM or CB in the body fluids and the concentration of FLM or CB in the composition during the storage can be kept high. When the amount of the nonionic, water-soluble cellulose derivative used is 5 w/v % or less, the obtained emulsion has a low viscosity to make the administration thereof easy and a comfortable feeling is recognized when the emulsion is used as eye drops. It is preferable to use the amount of the nonionic, water-soluble cellulose derivative in the range of 0.025 to 0.5 w/v % since the obtained emulsion shows particularly high stability of the dissolution concentration of FLM or CB in the body fluids and the concentration of FLM or CB.

The chelating agents, polycarboxylic acid compounds and pharmaceutically acceptable salts thereof used in the present invention are not particularly limited. They include, for example, ethylenediamine-tetraacetic acid (EDTA), citric acid, thiomalic acid, L-glutamic acid, succinic acid, malonic acid, maleic acid, dl-malic acid, adipic acid, tartaric acid, D-tartaric acid, fumaric acid, L-aspartic acid, glycyrrhizic acid, hydroxyethylethylenediaminetriacetic acid, diethylenetriamine-pentaacetic acid and pharmaceutically acceptable salts of them, and L-cystine. At least one of the group consisting of these chelating agents, polycarboxylic acid compounds and pharmaceutically acceptable salts thereof is incorporated into the emulsion of the present invention. Among these chelating agents, polycarboxylic acid compounds and pharmaceutically acceptable salts thereof, EDTA, citric acid and pharmaceutically acceptable salts thereof, which are widely used for eye drops, are preferred.

The pharmaceutically acceptable salts of EDTA usable in the present invention are, for example, sodium edetate (disodium edetate), tetrasodium edetate (tetrasodium edetate dihydrate), tetrasodiuin edetate tetrahydrate and calcium disodium edetate. Examples of the pharmaceutically acceptable salts of citric acid usable in the present invention are sodium citrate (trisodium citrate), disodium citrate (dibasic sodium citrate), trisodium citrate, sodium dihydrogen citrate, calcium citrate, dipotassium hydrogen citrate, potassium dihydrogen citrate and tripotassium citrate monohydrate.

The chelating agent, polycarboxylic acid compound and pharmaceutically acceptable salt thereof are used each in an amount of usually 0.0001 to 0.2 w/v %, preferably 0.0004 to 0.18 w/v %, more preferably 0.0005 to 0.18 w/v %, and most preferably 0.0025 to 0.05 w/v %. When the amount of the chelating agent, polycarboxylic acid compound and pharmaceutically acceptable salt thereof is 0.0001 w/v % or higher, the dissolution concentration of each of FLM and CB in the body fluids and the stability of the concentration of FLM and CB during the storage are high. When the amount of the chelating agent, polycarboxylic acid compound and pharmaceutically acceptable salt thereof is 0.2 w/v % or less, the stability of the emulsion is high. The amount of the chelating agent, polycarboxylic acid compound and pharmaceutically acceptable salt thereof in the range of 0.0025 to 0.05 w/v % is preferable. Because the obtained emulsion shows a particularly high stability of the dissolution concentration of FLM or CB in the body fluids and of the concentration of FLM or CB during the storage. In addition, this emulsion is free from the color change and oil drop formation (or oil separation) during the storage.

The drug in the emulsion of the present invention is FLM or CB, and the concentration thereof is usually 0.001 to 0.5 w/v %, preferably 0.005 to 0.1 w/v %. When the concentration of FLM or CB is 0.001 w/v % or higher, the dissolution concentration thereof in the body fluids is high. When the concentration of FLM or CB is 0.5 w/v % or less, this drug is not easily crystallized during the storage. The concentration of FLM or CB in the range of 0.005 to 0.1 w/v % is preferred because the obtained emulsion shows a particularly high stability of the dissolution concentration of FLM or CB in the body fluids and of the concentration of FLM or CB during the storage.

The phospholipids used in the present invention are not particularly limited. They are, for example, yolk lecithin, soybean lecithin, as well as lyso-forms and hydrogenated products thereof, phosphatidylcholine, phosphatidylethanolamine, phosphatidylserine, phosphatidylinositol, phosphatidylglycerol, dicetyl phosphate, sphingomyelin; synthetic phospholipids such as dimyristoyl phosphatidylcholine, dip almitoyl phosphatidylcholine and distearoyl phosphatidylcholine; and mixtures of these phospholipids. At least one phospholipid selected from among the above-described group of the phospholipids is incorporated into the emulsion of the present invention.

These phospholipids are easily available on the market under the trade names of, for example, Coatsome (registered trademark) NC-10S (high purity yolk lecithin; a product of NOF Corporation), purified egg yolk lecithin (Asahi Chemical Industry Co., Ltd.), Egg yolk lecithin PL-100H, ditto PL-100E, ditto PL-100LE and ditto PC-98N (Q. P. Corporation), Powdery egg yolk lecithin (hydrogenated and purified yolk lecithin) R-27, ditto R-20 and ditto R-5 (Asahi Chemical Industry Co., Ltd.), PCS (soybean phosphatidylcholine; Nippon Fine Chemical Co., Ltd.), PCSH (hydrogenated soybean phosphatidylcholine; Nippon Fine Chemical Co., Ltd.), Coatsome (registered trademark) NC-21 (hydrogenated soybean lecithin; NOF Corporation), Egg yolk lecithin LPL-20 (Q. P. Corporation), Coatsome (registered trademark) MC-6060 (L-α-dipalmitoyl phosphatidylcholine; NOF Corporation), Coatsome (registered trademark) MA-6060 (L-α-dipalmitoyl phosphatidic acid; NOF Corporation), Coatsome (registered trademark) MGLS-6060 (Na salt of L-α-dipalmitoyl phosphatidyl-DL-glycerol; NOF Corporation), Coatsome (registered trademark) MGLA-6060 (NH, salt of L-α-dipalmitoyl phosphatidyl-DL-glycerol; NOF Corporation), Sphingolipid CB-1 (a sphingolipid; Q. P. Corporation), etc.

When FLM is incorporated as the drug into the emulsion of the present invention, the amount of the phospholipid used is usually 10 to 150 parts by weight, preferably 20 to 100 parts by weight and more preferably 40 to 100 parts by weight, per one part by weight of FLM. In case the phospholipid is contained in the emulsion in an amount of at least 10 parts by weight per one part by weight of FLM, FLM is not easily crystallized during the storage. Also, by using the phospholipid in an amount of not larger than 150 parts by weight per one part by weight of FLM, the dissolution concentration of FLM in the body fluids is high. It is preferred to use phospholipid in an amount in the range of 40 to 100 parts by weight per one part by weight of FLM because the obtained emulsion has a particularly high stability of the dissolution concentration of FLM in the body fluids and of the concentration of FLM in the composition during the storage.

When CB is incorporated as the drug into the emulsion of the present invention, the amount of the phospholipid used is usually 5 to 100 parts by weight, preferably 10 to 80 parts by, per one part by weight of CB. By using the phospholipid in an amount of at least 5 parts by weight per one part by weight of CB, CB is not easily crystallized during the storage. Also, by using the phospholipid in an amount of not larger than 100 parts by weight per one part by weight of CB, the dissolution concentration of CB in the body fluids is high. It is preferable to use phospholipid in an amount in the range of 10 to 80 parts by weight per one part by weight of CB because the obtained emulsion has a particularly high stability of the dissolution concentration of CB in the body fluids and of the concentration of CB in the composition during the storage.

An emulsifying adjuvant may be added to the phospholipids. Examples of the emulsifying adjuvant include sterols such as cholesterol; aliphatic amines such as stearylamine; saturated and unsaturated fatty acids such as stearic acid, palmitic acid, myristic acid, linoleic acid and oleic acid; and pharmaceutically acceptable salts (such as sodium salts and potassium salts) of them. Although the amount of the emulsifying adjuvant is not particularly limited, usually it is not larger than 0.2 part by weight per one part by weight of the phospholipid. The oil used in the present invention is not particularly limited. The oils are, for example, vegetable oils such as soybean oil, sesame oil, corn oil, peanut oil, olive oil, safflower oil, jojoba oil, cotton seed oil and rapeseed oil; oils derived from animal oils and fats such as squalane; mono-, di- and triglycerides of fatty acids having 6 to 18 carbon atoms (such as caproic acid, stearic acid, palmitic acid, myristic acid and linoleic acid) such as glycerol tricaprylate and tricaprylin and mixtures of them; mineral oils such as liquid paraffin and light liquid paraffin; silicone oil; and fatty acid esters. The viscosity and specific gravity of these oils are not particularly limited. The oils having any viscosity and specific gravity are usable in the present invention. At least one of the oils of the above-described group is incorporated into the emulsion of the present invention.

These oils are easily available on the market under the trade names of Purified soybean oil (Showa Sangyo Co., Ltd.), Purified olive oil (Showa Sangyo Co., Ltd.), NIKKOL Safflower Oil (Nikko Chemicals Co., Ltd.), NIKKOL Jojoba Oil E (Nikko Chemicals Co., Ltd.), NIKKOL Triester F-810 (medium-length chain fatty acid triglycerides; Nikko Chemicals Co., Ltd.), Panasate. 810 (medium-length chain fatty acid triglycerides; NOF Corporation), NIKKOL Trifat P-52 (hydrogenated palm oil fatty acid triglycerides; Nikko Chemicals Co., Ltd.), NIKKOL MGS-A (glycerol monostearate; Nikko Chemicals Co., Ltd.), NIKKOL IPM-EX (isopropyl myristate; Nikko Chemicals Co., Ltd.), NIKKOL IPP (isopropyl palmitate; Nikko Chemicals Co., Ltd.), Toray Dow Corning Silicone SH20OC-100cs (Toray Dow Corning Silicone Corp., Light Liquid Paraffin No. 70-S, Liquid Paraffin No. 150-S, Liquid Paraffin No. 260-S and Liquid Paraffin No. 350-S (Sanko Chemical Industry Co. Ltd.).

Among these oils, the liquid paraffin is preferred because the color change of the emulsion during the storage is only slight when it is used.

When FLM is incorporated as the active ingredient, the amount of the oil used is usually 0.5 to 20 parts by weight, preferably 1 to 10 parts by weight, per one part by weight of the phospholipid, and the oil concentration in the emulsion is preferably not higher than 25 w/v %. When the amount of the oil used together with FLM is in the range of 0.5 to 20 parts by weight per one part by weight of the phospholipid, the stability of the emulsion during the storage is high. When the amount of the oil used together with FLM is at least 0.5% by weight per one part by weight of the phospholipid, the color change during the storage is only slight. The oil concentration in the emulsion is preferably 25 w/v % or below because an emulsion having a low viscosity can be obtained, which can be easily administered, and when the emulsion is used as eye drops, a comfortable feeling is realized upon the application.

When CB is incorporated. as the active ingredient, the amount of the oil used is usually 0.5 to 80 parts by weight, preferably 0.5 to 50 parts by, per one part by weight of the phospholipid, and the oil concentration in the emulsion is preferably not higher than 25 w/v %. When the amount of the oil used together with CB is in the range of 0.5 to 80 parts by weight per one part by weight of the phospholipid, the stability of the emulsion during the storage is high and oil drops are not formed during the storage. When the amount of the oil used together with CB is at least 0.5 % by weight per one part by weight of the phospholipid, the color change during the storage is only slight. The oil concentration in the emulsion is preferably 25 w/v % or below because an emulsion having a low viscosity can be obtained, which can be easily administered, and when the emulsion is used as eye drops, a comfortable feeling is realized upon the application.

In preparing the emulsion of the present invention, additives may be added to the indispensable components, i. e. water, oil or phospholipid so far as the effect of the present invention is not impaired. The additives are isotonicity agents such as sugars, e.g. xylitol, mannitol, sorbitol and glucose, and polyhydric alcohols, e.g. propylene glycol and glycerol; pH adjusting agents such as sodium hydroxide and hydrochloric acid; preservatives such as parabens, e. g. methyl p-hydroxybenzoate and propyl p-hydroxybenzoate, sorbic acid and pharmaceutically acceptable salts thereof, benzyl alcohol, phenethyl alcohol, benzethonium chloride, benzalkonium chloride, chlorhexidine gluconate, hydroxyquinoline sulfate, chlorobutanol and thimerosal; thickening agents such as synthetic polymers, e.g. polyvinylpyrrolidone, polyvinyl alcohol and sodium polyacrylate, high-molecular protein materials, e.g. gelatin, and polysaccharides, e.g. dextran, carrageenan, sodium chondroitin sulfate, xantham gum, gum arabic, Karaya gum and locust bean gum; antioxidants such as ascorbic acid, sodium hydrogensulfite, sodium thioglycolate and α-thioglycerol; and buffering agents such as acetic acid, phosphoric acid and pharmaceutically acceptable salts of them, monoethanolamine, triethanolamine, boric acid, borax, sodium carbonate, sodium hydrogen carbonate, aminoethyl sulfonic acid, ε-aminocaproic acid, sodium chloride and potassium chloride.

Further, at least one stabilizer selected from the group consisting of amino acids and pharmaceutically acceptable salts thereof, tocopherol and derivatives thereof and sucrose fatty acid esters, can be added to one of the indispensable components, i. e. water, oil and phospholipid, of the present invention.

Examples of amino acids usable in the present invention include cysteine, histidine, pharmaceutically acceptable salts (such as hydrochlorides) of them, methionine, phenylalanine, serine and the like.

Examples of the tocopherol derivatives usable in the present invention include tocopherol acetate, tocopherol nicotinate, tocopherol succinate and the like.

The pH of the emulsion of the present invention is usually controlled in the range of 3 to 10. From the viewpoint of the irritation, the pH range is preferably 5 to 9. When the emulsion is used as eye drops, pH range is preferably 5.5 to 8.0.

The emulsion of the present invention can be sterilized by the filtration sterilization method with a membrane or by the heating sterilization method.

The emulsion of the present invention can be filled into a plastic eye drop bottle to use it as eye drops. In order to stably store the emulsion for a long period of time, the emulsion may be packed into a bag made of a laminate of a polyethylene film and an aluminum foil by 0 the pillow type packaging method together with a deoxidizer [such as Ageless (registered trademark) SA, and Ageless Z; Mitsubishi Gas Chemical Co., Ltd.].

The emulsion of the present invention can be filled into a plastic dropping bottle to use it as ear drops. In order to stably store the emulsion for a long period of time, the emulsion may be packed into a bag made of a laminate of a polyethylene film and an aluminum foil by the pillow type packaging method together with a deoxidizer [such as Ageless (registered trademark) SA, and Ageless Z; Mitsubishi Gas Chemical Co., Ltd.].

The emulsion of the present invention can be packed into a quantitative nasal nebulizer to use it as nasal drops. In order to stably store the emulsion for a long period of time, the emulsion may be packed into a bag made of a laminate of a polyethylene film and an aluminum foil by the pillow type packaging method together with a disoxidant [such as Ageless (registered trademark) SA, and Ageless Z; Mitsubishi Gas Chemical Co., Ltd.].

The emulsion of the present invention can be fed into an ampoule and the ampoule is sealed by fusion to obtain an injection (such as intravenous injection, arterial injection, hypodermic injection, intradermal injection, intramuscular injection, intraspinal injection, intraperitoneal injection, intraocular injection and the like), a liquid for internal use, an inhalation or a aerosol. The product thus obtained is fed into a suitable container selected depending on the use, such as a plastic bottle for the liquid for internal use, electric nebulizer for the inhalation, an atomizer for aerosol and the like.

The description will be made on the methods for preparing the emulsion of the present invention. Various well-known methods can be employed for preparing the emulsion of the present invention. For example, yolk lecithin, if desired a phospholipid such as phosphatidylethanolamine and an emulsifying adjuvant such as oleic acid, and FLM or CB are dissolved in a suitable organic solvent such as hexane or ethanol under stirring. Then, the solvent is evaporated under reduced pressure to prepare a thin lipid membrane. An oil and an aqueous solution prepared by dissolving a non-ionic, water-soluble cellulose derivative and optionally at least one selected from the group consisting of a chelating agent, polycarboxylic acid compounds and pharmaceutically acceptable salts thereof as well as various additives such as an antiseptic and an isotonicity agent in water, are added to the thin lipid membrane. They are vigorously stirred by agitation to conduct the pre-emulsification. The pre-emulsion thus obtained is emulsified with an ordinary emulsifying machine. After the completion of the emulsification, HCl or NaOH is added to the emulsion to adjust it to an intended pH, and thereby to obtain the O/W emulsion containing FLM or CB of the present invention. The emulsion is filtered and fed into a suitable container through a membrane filter and then sterilized to obtain the emulsion of the present invention.

When FLM is used as the active ingredient, the intended FLM-containing O/W emulsion of the present invention can be obtained by preparing an O/W emulsion comprising FLM, a phospholipid, an oil and water in the same manner as that described above, adding an aqueous solution containing a nonionic, water-soluble cellulose derivative and optionally at least one of a chelating agent, polycarboxylic acid compounds and pharmaceutically acceptable salts thereof, an antiseptic agent, an isotonicity agent and the like to the emulsion, and stirring the obtained mixture.

EXAMPLES

The following Example will further illustrate the present invention, wherein the emulsion is to be used as eye drops. Determination of solubility of active ingredient in lachrymal fluid:

As descried in the above "Background of the Invention", the bioavailability can be improved by increasing the concentration of the administered, hardly soluble active ingredient in the body fluids. In case of eye drops, it is known that the bioavailability can be improved by increasing the concentration of the hardly soluble active ingredient in the lachrymal fluid immediately after the application. The concentration of the active ingredient in the lachrymal fluid can be one of the indexes for determining the degree of improvement in the ransfer of the hardly soluble active ingredient into the eye tissue. ecause the active ingredient applied to the eye is rapidly excreted rom the eye surface which is the main absorption region by the turnover of the lachrymal fluid, etc., a method capable of instantaneously determining the quantity of FLM or CB dissolved in the lachrymal fluid must be employed in the determination of the solubility of FLM or CB in the lachrymal fluid.

The solubility of FLM or CB in the lachrymal fluid was determined by determining the concentration of FLM or CB dissolved in an artificial lachrymal fluid (PBS) (hereinafter referred to as "FLM dissolution concentration" or "CB dissolution concentration" according to a drug dissolution test method described in "Example" in WO 97/05882, p.10. In the determination of FLM dissolution concentration or CB dissolution concentration, a dilution rate of 1/51 with PBS was selected for the FLM-containing emulsion and that of 1/41 with PBS was selected for CB-containing emulsion on the basis of the dilution rates described in the drug dissolution test method.

Dissolution Tests of FLM and CB

As the artificial lachrymal fluid used in place of the human lachrymal fluid, PBS usually used for biochemical tests (composition: 0.8 w/v % of NaCl, 0.02 w/v % of KCl, 0.115 w/v % of $Na_2HPO_4$ and 0.02 w/v % of $KH_2PO_4$, pH7.4) was used. PBS was fed into a 15 mL test tube with a lid and then kept in a water bath at 36° C. Then, a predetermined amount of the emulsion was added to PBS, and they were gently and invertibly shaken at room temperature for 30 seconds. The amounts of the emulsion and PBS were as shown below:

| Dilution rate | | PBS (mL) |
|---|---|---|
| | FLM-containing emulsion (mL) | |
| 1/51 | 0.1 | 5.0 |
| | CB-containing emulsion (mL) | |
| 1/41 | 0.25 | 10.0 |

PBS (0.4 mL) containing the emulsion was rapidly (within 3 minutes after the addition of the emulsion to PBS) poured in an ultrafiltration kit [Ultrafree (registered trademark)-MC (Cat. No. UFC3LTK00); Millipore Corporation]. Then PBS containing FLM or CB dissolved therein was separated from the emulsion with a centrifugal separator (MS-150; Tomy Seiko Co., Ltd.) (8500 rpm, 5 minutes). The HPLC analysis was used to quantitate FLM or CB present in the separated PBS to determine the dissolution concentration of FLM or CB.

Determination of stability as for solubility of active ingredient in lachrymal fluid and concentration of active ingredient during storage:

The stability of solubility of each FLM and CB in the lachrymal fluid and the concentration of each FLM and CB during the storage were evaluated as described below.

5 mL of a sample was fed into a 5 mL white glass ampoule, which was then sealed by fusion and stored at 40° C. or 60° C. After the storage at such a temperature for a predetermined period of time, FLM dissolution concentration, CB dissolution concentration, FLM concentration and CB concentration were determined. When the values obtained after the storage was 90% or higher based on the values obtained before the storage, the results were evaluated to be stable.

EXAMPLE 1

Egg yolk lecithin [Coatsome (registered trademark) NC-10S, 95% phosphatidylcholine; NOF Corporation; hereinafter referred to as "EPC"] and purified egg yolk lecithin (70% phosphatidylcholine and 20% phosphatidylethanolamine; Asahi Chemical Industry Co., Ltd.; hereinafter referred to as "PYL") in a weight ratio of 7:3 were dissolved in a mixture of hexane/ethanol [10/1 (v/v)] under stirring. Separately, FLM was dissolved in ethanol, and the obtained solution was mixed under stirring with the phospholipid solution obtained as described above. Then, the solvent was evaporated with an evaporator and then with a vacuum pump to form a thin phospholipid membrane containing FLM.

Methylcellulose [Metolose (registered trademark) SM-400 (Shin-Etsu Chemical Co., Ltd.)] or Hydroxypropylmethylcellulose [Metolose (registered trademark) 60SH- 4000 (Shin-Etsu Chemical Co., Ltd.)] was dispersed in hot water (70° C. or higher) to obtain a hot, homogeneous aqueous slurry, which was then cooled under stirring to obtain a solution. Glycerol was dissolved in the resultant solution to obtain an aqueous glycerol solution containing methylcellulose or hydroxypropylmethyl-cellulose.

The obtained aqueous solution and liquid paraffin (No. 260-S; Sanko Chemical Industry Co. Ltd.) were added to the thin phospholipid membrane prepared as described above, and they were stirred by vigorously shaking to conduct the pre-emulsification. Distilled water was added to the pre-emulsified liquid to make the total amount 100 mL. The obtained mixture was emulsified by passing through a microfluidizer (M-110EH; Microfluidics Co.) 30 times under a pressure of 750 kg/cm$^2$. After the completion of the emulsification, 1 N NaOH was added to the emulsion to adjust pH thereof to 6.5–7.5 to obtain the FLM-containing O/W emulsion (hereinafter referred to as "FLM emulsion") of the present invention. The formulation of the emulsion is shown in Table 1.

EXAMPLE 2

An FLM emulsion of the present invention was obtained in the same manner as that of Example 1 except that EDTA disodium salt or sodium citrate was dissolved, under stirring, in the aqueous glycerol solution containing methylcellulose or hydroxypropylmethylcellulose. The formulation is shown in Table 1.

Comparative Example 1

An FLM emulsion was obtained in the same manner as that of Example 1 except that methylcellulose and hydroxypropylmethylcellulose were not added. The formulation is shown in Table 1.

Comparative Example 2

An FLM emulsion was obtained in the same manner as that of Example 2 except that methylcellulose and hydroxypropylmethylcellulose were not added. The formulation is shown in Table 1.

TABLE 1

| | Phospholipid w/v % | Liquid paraffin w/v % | FLM conc. w/v % | Nonionic water-soluble cellulose derivative w/v % | Polycarboxylic acid compound and chelating agent w/v % |
|---|---|---|---|---|---|
| Ex. 1 | | | | | |
| 1 | 2.0 | 10.0 | 0.02 | MC 0.10 | — |
| 2 | 2.0 | 10.0 | 0.02 | HPMC 0.10 | — |
| Ex. 2 | | | | | |
| 1 | 2.0 | 10.0 | 0.02 | MC 0.10 | EDTA 0.05 |
| 2 | 2.0 | 10.0 | 0.02 | MC 0.10 | Cit 0.10 |
| 3 | 2.0 | 10.0 | 0.02 | HPMC 0.10 | EDTA 0.05 |
| 4 | 2.0 | 10.0 | 0.02 | HPMC 0.10 | Cit 0.10 |
| Comp. Ex. 1 | | | | | |
| 1 | 2.0 | 10.0 | 0.02 | — | |
| Comp. Ex. 2 | | | | | |
| 1 | 2.0 | 10.0 | 0.02 | — | EDTA 0.05 |
| 2 | 2.0 | 10.0 | 0.02 | — | Cit 0.10 |

MC: methylcellulose [Metolose (registered trademark) SM-400 (Shin-Etsu Chemical Co., Ltd.)]
HPMC: hydroxypropylmethylcellulose [Metolose 60SH-4000 (Shin-Etsu Chemical Co., Ltd.)]
Liquid paraffin: Liquid paraffin No. 260-S (Sanko Chemical Industry Co. Ltd.
EDTA: ethylenediaminetetraacetic acid disodium salt Cit: sodium citrate
Phospholipid: EPC:PYL=7:3 (weight ratio)
Each formulation contains 2.2 w/v % of glycerol Test Example 1

The FLM dissolution tests and tests on the stability of FLM dissolution concentration and of FLM concentration during the storage, of each of the emulsions of the present invention obtained in Examples 1 and 2 and the emulsions obtained in Comparative Examples 1 and 2 were conducted by methods of "Determination of solubility of active ingredient in lachrymal fluid" and "Determination of stability as for solubility of active ingredient in lachrymal fluid and concentration of active ingredient during storage" described above. Table 2 shows the FLM dissolution concentrations in FLM emulsions of the present invention obtained in Examples 1 and 2 and that in FLM emulsions obtained in Comparative Examples 1 and 2, and also the results of the stability test of the emulsions after the storage at 60° C for one and two weeks. For comparison, the FLM dissolution concentrations in commercially available FLM suspensions [Flumetholon (registered trademarks) 0.02 and 0.1; Santen Pharmaceutical Co., Ltd.] are also shown.

The FLM emulsions of the present invention have remarkably higher FLM dissolution concentrations than those obtained in Comparative Examples. The FLM dissolution concentration and FLM concentration were stable after the storage at 60° C. for one week. Particularly, the FLM emulsions of the present invention containing EDTA disodium salt or sodium citrate were stable on FLM dissolution concentration and FLM concentration even after the storage at 60° C. for two weeks.

TABLE 2

| | | Storage storability | | | |
|---|---|---|---|---|---|
| | FLM | Storage (60°C., 1 week) | | Storage (60°C., 2 weeks) | |
| | dissolution conc. μg/ml | FLM conc. | FLM dissolution conc. | FLM conc. | FLM dissolution conc. |
| Ex. 1 | | | | | |
| 1 | 2.42 | ○ | ○ | ○ | x |
| 2 | 2.54 | ○ | ○ | ○ | x |
| Ex. 2 | | | | | |
| 1 | 2.44 | ○ | ○ | ○ | ○ |
| 2 | 2.45 | ○ | ○ | ○ | ○ |
| 3 | 2.48 | ○ | ○ | ○ | ○ |
| 4 | 2.57 | ○ | ○ | ○ | ○ |
| Comp. Ex. 1 | 1.62 | x | x | x | x |
| Comp. Ex. 2 | | | | | |
| 1 | 2.02 | ○ | x | x | x |
| 2 | 2.08 | x | x | x | x |
| Suspension (Flumetholon 0.02) | 0.73 | — | — | — | — |
| Suspension (Flumetholon 0.1) | 1.54 | — | — | — | — |

Dissolution test: FLM emulsion was diluted to a concentration of 1/51 with PBS.

Storage stability:
  o: stable (at least 90% based on the value before the storage);
  X: unstable (less than 90% based on the value before the storage)

Suspension: Flumetholon (registered trademarks) 0.02 and 0.1 (FLM suspended eye drop, 0.02 and 0.1 w/v % FLM, Santen Pharmaceutical Co., Ltd.).

EXAMPLE 3

An FLM emulsion of the present invention was prepared in the same manner as that of Example 2 except that Liquid paraffin No. 200-S (Sanko Chemical Industry Co. Ltd.) was used as an oil and Metolose (registered trademark) SM-100 (Shin-Etsu Chemical Co., Ltd.) was used as methylcellulose. The formulation is shown in Table 3.

Comparative Example 3

An FLM emulsion was prepared in the same manner as that of Example 3 except that methylcellulose was not used. The formulation is shown in Table 3.

TABLE 3

| | Phospholipid w/v % | Liquid paraffin w/v % | FLM conc. w/v % | Methylcellulose w/v % | EDTA w/v % |
|---|---|---|---|---|---|
| Ex. 3 | 9.0 | 25.0 | 0.1 | 0.5 | 0.008 |
| Comp. Ex. 3 | 9.0 | 25.0 | 0.1 | — | — |

Liquid paraffin: Liquid paraffin No. 200-S (Sanko Chemical Industry Co. Ltd.)
Methylcellulose: Metolose (registered trademark) SM-100 (Shin-Etsu Chemical Co., Ltd.)
EDTA: ethylenediaminetetraacetic acid disodium salt
Phospholipid: EPC:PYL=7:3 (weight ratio)
Each formulation contains 2.0 w/v % of glycerol Test Example 2

The FLM dissolution tests and tests on the stability of FLM dissolution concentration and of FLM concentration during the storage of the FLM emulsion of the present invention obtained in Example 3 and the FLM emulsion of Comparative Example 3 were conducted in the same manner as that of Test Example 1. Table 4 shows the dissolution concentrations of the FLM emulsion of the present invention obtained in Example 3 and the FLM emulsion obtained in Comparative Example 3 and also the results of the stability test of the emulsions obtained after the storage at 40° C. for four weeks. For comparison, the FLM dissolution concentration of the commercially available FLM suspension [Flumetholon (registered trademarks) 0.1; Santen Pharmaceutical Co., Ltd.] is also shown.

The FLM emulsion of the present invention had a remarkably higher FLM dissolution concentration than that obtained in the Comparative Example. The FLM dissolution concentration and FLM concentration were stable after the storage at 40° C. for four weeks.

TABLE 4

| | FLM dissolution conc. µg/ml | Storage stability (40°C., 4 weeks) | |
|---|---|---|---|
| | | FLM conc. | FLM dissolution conc. |
| Ex. 3 | 6.71 | o | o |
| Comp. Ex. 3 | 4.40 | o | x |
| Suspension (Flumetholon 0.1) | 1.54 | — | — |

Dissolution test: FLM emulsion was diluted to a concentration of 1/51 with PBS.

Storage stability:
  o: stable (at least 90% based on the value before the storage);
  X: unstable (less than 90% based on the value before the storage)

Suspension: Flumetholon (registered trademarks) 0.1 (FLM suspended eye drop, 0.1 w/v % FLM, Santen Pharmaceutical Co., Ltd.).

EXAMPLE 4

An FLM emulsion of the present invention comprising FLM, a phospholipid (weight ratio of EPC:PYL =7:3), liquid paraffin (No. 150-S; Sanko Chemical Industry Co. Ltd.), soybean oil (Wako Pure Chemical Industries, Co., Ltd.), Panasate 810 (NOF Corporation), corn oil (SIGMA Chemical Company) or tricaprylin (Wako Pure Chemical Industries, Co., Ltd.) as the oils, methylcellulose [Metolose (registered trademark) SM-100; Shin-Etsu Chemical Co., Ltd.], EDTA disodium salt, glycerol and water was prepared in the same manner as that of Example 2. The formulation is shown in Table 5.

TABLE 5

| | Phospholipid w/v % | Oil | | FLM conc. w/v % | Methylcellulose w/v % | EDTA w/v % |
|---|---|---|---|---|---|---|
| Ex. 4 | | | | | | |
| 1 | 1.4 | Liquid paraffin | 7.0 | 0.02 | 0.1 | 0.01 |
| 2 | 1.4 | Soybean oil | 7.0 | 0.02 | 0.1 | 0.01 |
| 3 | 1.4 | Panasate8 | 7.0 | 0.02 | 0.1 | 0.01 |
| 4 | 1.4 | Corn oil | 7.0 | 0.02 | 0.1 | 0.01 |
| 5 | 1.4 | Tricaprylin | 7.0 | 0.02 | 0.1 | 0.01 |

Liquid paraffin: Liquid paraffin No. 150-S (Sanko Chemical Industry Co. Ltd.
Soybean oil: Wako, the first grade (Wako Pure Chemical Industries, Co., Ltd.)
Panasate 810: medium chain fatty acid triglyceride (NOF Corporation)
Corn oil: SIGMA CHEMICAL COMPANY
Tricaprylin (Wako Pure Chemical Industries, Co., Ltd.)
Methylcellulose: Metolose SM-100 (Shin-Etsu Chemical Co., Ltd.)
EDTA: ethylenediaminetetraacetic acid disodium salt
Phospholipid: EPC:PYL=7:3 (weight ratio)
Each Formulation contains 2.2 w/v % of glycerol Test Example 3

The FLM dissolution tests and tests on the stability of FLM dissolution concentration and of FLM concentration during the storage of the FLM emulsion of the present invention obtained in Example 4 were conducted in the same manner as that of Test Example 1. Table 6 shows the FLM dissolution concentrations of the FLM emulsion of the present invention obtained in Example 4 and also the results of the stability test after the storage at 60° C. for two weeks.

All the FLM emulsions of the present invention obtained by using various oils had high FLM dissolution concentrations. The FLM dissolution concentration and FLM concentration were stable after the storage at 60° C. for two weeks.

TABLE 6

| | FLM dissolution conc. μg/ml | Storage stability (60°C., 2 weeks) | |
|---|---|---|---|
| | | FLM conc. | FLM dissolution conc. |
| Ex. 4 | | | |
| 1 | 3.33 | ○ | ○ |
| 2 | 2.79 | ○ | ○ |
| 3 | 2.69 | ○ | ○ |
| 4 | 2.81 | ○ | ○ |
| 5 | 2.67 | ○ | ○ |

Dissolution test: FLM emulsion was diluted to a concentration of 1/51 with PBS.

Storage stability:
  ○: stable (at least 90% based on the value before the storage);
  X: unstable (less than 90% based on the value before the storage)

EXAMPLE 5

An FLM emulsion of the present invention comprising FLM, a phospholipid (weight ratio of EPC:PYL=7:3), liquid paraffin (No. 150-S; Sanko Chemical Industry Co. Ltd.), methylcellulose [Metolose (registered trademark) SM-100; Shin-Etsu Chemical Co., Ltd.], EDTA disodium salt, glycerol and water was prepared in the same manner as that of Example 2. The formulation is shown in Table 7.

Test Example 4

The FLM dissolution tests and tests on the stability of FLM dissolution concentration and of FLM concentration during the storage of the FLM emulsion of the present invention obtained in Example 5 were conducted in the same manner as that of Test Example 1. Table 8 shows the FLM dissolution concentrations of the FLM emulsions of the present invention obtained in Examples 2-1, 4-1 and 5 and also the results of the stability test obtained after the storage at 60° C. for two weeks.

All the FLM emulsions of the present invention containing 0.001 to 0.5 w/v % of methylcellulose and 0.0004 to 0.18 w/v % of EDTA disodium salt had high FLM dissolution concentrations. The FLM dissolution concentration and FLM concentration were stable after the storage at 60° C. for two weeks.

TABLE 8

| | FLM dissolution conc. μg/ml | Storage stability (60°C., 2 weeks) | |
|---|---|---|---|
| | | FLM conc. | FLM dissolution conc. |
| Ex. 2 | | | |
| 1 | 2.44 | ○ | ○ |
| Ex. 4 | | | |
| 1 | 3.33 | ○ | ○ |
| Ex. 5 | | | |
| 1 | 0.76 | ○ | ○ |
| 2 | 1.98 | ○ | ○ |
| 3 | 2.61 | ○ | ○ |

Dissolution test: FLM emulsion was diluted to a concentration of 1/51 with PBS.

Storage stability:
  ○: stable (at least 90% based on the value before the storage);
  X: unstable (less than 90% based on the value before the storage)

TABLE 7

| | | Phospholipid w/v % | Liquid paraffin w/v % | FLM conc. w/v % | Lip/FLM | LP/Lip | Methylcellulose w/v % | EDTA w/v % |
|---|---|---|---|---|---|---|---|---|
| Ex. 2 | 1 | 2.0 | 10.0 | 0.02 | 100 | 5 | 0.1 | 0.05 |
| Ex. 4 | 1 | 1.4 | 7.0 | 0.02 | 70 | 5 | 0.1 | 0.01 |
| Ex. 5 | 1 | 0.2 | 0.2 | 0.005 | 40 | 1 | 0.01 | 0.0004 |
| | 2 | 1.4 | 7.0 | 0.02 | 70 | 5 | 0.001 | 0.05 |
| | 3 | 1.4 | 7.0 | 0.02 | 70 | 5 | 0.5 | 0.18 |

Liquid paraffin: Liquid paraffin No. 150-S (Sanko Chemical Industry Co. Ltd.)

Lip/FLM: phospholipid (w/v %)/FLM (w/v %)

LP/Lip: liquid paraffin (w/v %)/phospholipid (w/v %)

Methylcellulose: Metolose (registered trademark) SM-100 (Shin-Etsu Chemical Co., Ltd.)

EDTA: ethylenediaminetetraacetic acid disodium salt

Phospholipid: EPC:PYL=7:3 (weight ratio)

Each formulation contains 2.2 w/v % of glycerol

EXAMPLE 6

A CB-containing O/W emulsion of the present invention (hereinafter referred to as "CB emulsion"), a phospholipid (weight ratio of EPC:PYL =7:3), liquid paraffin (No. 150-S; Sanko Chemical Industry Co. Ltd.), methylcellulose [Metolose (registered trademark) SM-100; Shin-Etsu Chemical Co., Ltd.], glycerol and water was prepared in the same manner as that of Example 1. The formulation is shown in Table 9.

EXAMPLE 7

A CB-containing O/W emulsion of the present invention comprising CB, a phospholipid (weight ratio of EPC:PYL= 7:3), liquid paraffin (No. 150-S; Sanko Chemical Industry Co. Ltd.), methylcellulose [Metolose (registered trademark) SM-100; Shin-Etsu Chemical Co., Ltd.], EDTA disodium salt, glycerol and water was prepared in the same manner as that of Example 2. The formulation is shown in Table 9.

Comparative Example 4

A CB emulsion was prepared in the same manner as that of Example 6 except that methylcellulose was not added. The formulation is shown in Table 9.

Comparative Example 5

A CB emulsion was prepared in the same manner as that of Example 7 except that methylcellulose was not added. The formulation is shown in Table 9.

TABLE 9

|  | Phospholipid w/v % | Liquid paraffin w/v % | CB conc. w/v % | Methylcellulose w/v % | EDTA w/v % |
|---|---|---|---|---|---|
| Ex. 6 Ex. 7 | 0.84 | 4.2 | 0.018 | 0.2 | — |
| 1 | 0.84 | 4.2 | 0.018 | 0.2 | 0.01 |
| 2 | 0.2 | 9.0 | 0.02 | 0.1 | 0.01 |
| Comp. Ex. 4 | 0.84 | 4.2 | 0.018 | — | — |
| Comp. Ex. 5 | 0.84 | 4.2 | 0.018 | — | 0.01 |

Liquid paraffin: Liquid paraffin No. 150-S (Sanko Chemical Industry Co. Ltd.
Methylcellulose: Metolose (registered trademark) SM-100 (Shin-Etsu Chemical Co., Ltd.)
EDTA: ethylenediaminetetraacetic acid disodium salt
Phospholipid: EPC:PYL=7:3 (weight ratio) Each formulation contains 2.2 w/v % of glycerol Test Example 5

The CB dissolution tests and tests on the stability of CB dissolution concentration and on the stability of CB concentration during the storage of the CB emulsions of the present invention obtained in Examples 6 and 7 and Comparative Examples 4 and 5 were conducted in the same manner as that of Test Example 1. Table 10 shows the CB dissolution concentrations of the CB emulsions of the present invention obtained in Examples 6 and 7 and Comparative Examples 4 and 5 and also the results of the stability test after the storage at 40° C. for four weeks and 24 weeks. For comparison, the CB dissolution concentration of a commercially available CB suspension [CLOBURATE (registered trademark), 0.1 w/v % CB, Cusi (UK) Ltd.] was also shown.

All the CB emulsions of the present invention had high CB dissolution concentrations. The CB dissolution concentration and CB concentration were stable after the storage at 40° C. for 4 weeks. Particularly, the CB dissolution concentration and CB concentration of the CB emulsion of the present invention containing EDTA disodium salt were stable after the storage at 40° C. for 24 weeks.

TABLE 10

|  | Storage storability | | | | |
|---|---|---|---|---|---|
|  |  | Storage (40°C., 4 weeks) | | Storage (40°C., 24 weeks) | |
|  | CB dissolution conc. µg/ml | CB conc. | CB dissolution conc. | CB conc. | CB dissolution conc. |
| Ex. 6 Ex. 7 | 0.40 | ○ | ○ | x | x |
| 1 | 0.39 | ○ | ○ | ○ | ○ |
| 2 | 0.36 | ○ | ○ | ○ | ○ |
| Comp. Ex. 4 | 0.31 | ○ | x | x | x |
| Comp. Ex. 5 | 0.25 | ○ | x | x | x |
| Suspension | 0.17 | — | — | — | — |

Dissolution test: CB emulsion was diluted to a concentration of 1/41 with PBS.
Storage stability:
○: stable (at least 90% based on the value before the storage);
X: unstable (less than 90% based on the value before the storage)
Suspension: CLOBURATE (registered trademark), [CB-suspended eye drop, 0.1 w/v % CB, Cusi (UK) Ltd.]

Preparation Example 1

EPC, PYL and α-tocopherol acetate were dissolved in a mixture of hexane/ethanol [10/1 (v/v)] under stirring. Separately, FLM was dissolved in ethanol, and the obtained solution was mixed with the phospholipid solution, obtained as described above, under stirring. The solvent was evaporated with an evaporator and then with a vacuum pump to form a thin phospholipid membrane containing FLM.

Methylcellulose [Metolose (registered trademark) SM-400; Shin-Etsu Chemical Co., Ltd.] was dispersed in hot water (70° C. or higher) to obtain a hot homogeneous aqueous slurry, which was then cooled under stirring to obtain a solution. Polyvinylpyrrolidone [Kollidone (registered trademark) 30, BASF Aktiengesellschaft], glycerol, potassium sorbate and EDTA disodium salt were dissolved in the solution under stirring to obtain a solution of the water-soluble components.

The obtained solution of the water-soluble components and liquid paraffin (No. 260-S; Sanko Chemical Industry Co. Ltd.) were added to the thin phospholipid membrane prepared as described above, and they were vigorously shaken to conduct the pre-emulsification.

Distilled water was added to the pre-emulsified liquid to make the total quantity 1 L. The obtained mixture was emulsified by passing through a microfluidizer (M-110EH; Microfluidics Co.) 30 times under a pressure of 750 kg/cm². After the completion of the emulsification, 1 N NaOH was added to the emulsion to adjust pH thereof to 6.0. The emulsion was filtered through a membrane having a pore diameter of 0.45 µm to obtain an FLM emulsion of the present invention containing the above-described additives. The emulsion was fed into an eye drop bottle and sterilized by heating by the intermittent sterilization method to obtain the FLM-containing eye drops of the present invention. The eye drops of the present invention thus obtained were packed in a polyethylene film/aluminum foil laminate bag together with Ageless (registered trademark) Z (Mitsubishi Gas Chemical Co., Inc.) by the pillow type packaging method. The formulation was as follows:

Preparation 1

| Component | Amount and concentration |
|---|---|
| FLM | 0.02 w/v % |
| EPC | 0.98 w/v % |
| PYL | 0.42 w/v % |
| α-Tocopherol acetate | 0.065 w/v % |
| Liquid paraffin No. 260-S | 7.0 w/v % |
| Metolose (registered trademark) SM-400 | 0.1 w/v % |
| Disodium EDTA | 0.01 w/v % |
| Polyvinylpyrrolidone | 0.05 w/v % |
| Potassium sorbate | 0.1 w/v % |
| Glycerol | 2.2 w/v % |

Preparation Example 2

FLM-containing eye drops of the present invention were prepared in the same manner as that of the emulsion preparation method of Preparation Example 1 except that α-tocopherol acetate was not used, PCSH (hydrogenated soybean phosphatidyl choline; Nippon Fine Chemical Co., Ltd.) was further added as phospholipid and liquid paraffin No. 150-S (Sanko Chemical Industry Co. Ltd.) was used as oil. The product was packed in the same manner as that of Preparation Example 1. The formulation was as follows:

Preparation 2

| Component | Amount and concentration |
|---|---|
| FLM | 0.02 w/v % |
| EPC | 0.98 w/v % |
| PYL | 0.42 w/v % |
| PCSH | 0.14 w/v % |
| Liquid paraffin No. 150-S | 7.0 w/v % |
| Metolose (registered trademark) SM-400 | 0.1 w/v % |
| Disodium EDTA | 0.01 w/v % |
| Polyvinylpyrrolidone | 0.05 w/v % |
| Potassium sorbate | 0.1 w/v % |
| Glycerol | 2.2 w/v % |
| 1N HCl | suitable amount |

Preparation Example 3

FLM-containing eye drops of the present invention were prepared in the same manner. as that of the emulsion preparation method of Preparation Example 1 except that α-tocopherol acetate was not used, Coatsome (registered trademark) MC-6060 (L-α-dipalmitoyl phosphatidylcholine; NOF Corporation) was further added as the phospholipid, liquid paraffin No. 350-S (Sanko Chemical Industry Co. Ltd.) was used as oil and polyvinylpyrrolidone was replaced with gelatin (BACTO GELATIN; DIFCO LABORATORIES). The product was packed in the same manner as that of Preparation Example 1. The formulation was as follows:

Preparation 3

| Component | Amount and concentration |
|---|---|
| FLM | 0.02 w/v % |
| EPC | 0.98 w/v % |
| Coatsome (registered trademark) MC-6060 | 0.14 w/v % |
| PYL | 0.42 w/v % |
| Liquid paraffin No. 350-S | 7.0 w/v % |
| Metolose (registered trademark) SM-400 | 0.1 w/v % |
| Disodium EDTA | 0.01 w/v % |
| Gelatin | 0.05 w/v % |
| Potassium sorbate | 0.1 w/v % |
| Glycerol | 2.2 w/v % |

Preparation Example 4

FLM-containing eye drops of the present invention were prepared in the same manner as that of the emulsion preparation method of Preparation Example 1 except that α-tocopherol acetate was not used, Coatsome (registered trademark) NC-21 (hydrogenated soybean lecithin; NOF Corporation) was further added as the phospholipid, light liquid paraffin No. 70-S (Sanko Chemical Industry Co. Ltd.) was used as oil, Metolose (registered trademark) SM-100 (Shin-Etsu Chemical Co., Ltd.) was used as methylcellulose, polyvinylpyrrolidone was replaced with a polyvinyl alcohol (degree of polymerization: about 2,000; Wake Pure Chemical Industries, Co., Ltd.) and potassium sorbate was replaced with benzyl alcohol. The product was packed in the same manner as that of Preparation Example 1. The formulation was as follows:

Preparation 4

| Component | Amount and concentration |
|---|---|
| FLM | 0.02 w/v % |
| EPC | 0.98 w/v % |
| Coatsome (registered trademark) NC-21 | 0.14 w/v % |
| PYL | 0.42 w/v % |
| Light liquid paraffin No. 70-S | 7.0 w/v % |
| Metolose (registered trademark) SM-100 | 0.1 w/v % |
| Disodium EDTA | 0.01 w/v % |
| Polyvinyl alcohol | 0.05 w/v % |
| Benzyl alcohol | 0.5 w/v % |
| Glycerol | 2.2 w/v % |

Preparation Example 5

FLM-containing eye drops of the present invention were prepared in the same manner as that of the emulsion preparation method of Preparation Example 1 except that α-tocopherol acetate was not used, egg yolk lecithin LPL-20 (Q. P. Corporation) was further added as the phospholipid, Metolose (registered trademark) SM-1500 (Shin-Etsu Chemical Co., Ltd.) was used as methylcellulose and potassium sorbate was replaced with benzyl alcohol. The product was packed in the same manner as that of Preparation Example 1. The formulation was as follows:

Preparation 5

| Component | Amount and concentration |
|---|---|
| FLM | 0.02 w/v % |
| EPC | 0.98 w/v % |
| Egg yolk lecithin LPL-20 | 0.14 w/v % |
| PYL | 0.42 w/v % |
| Liquid paraffin No. 260-S | 7.0 w/v % |
| Metolose (registered trademark) SM-1500 | 0.1 w/v % |
| Disodium EDTA | 0.01 w/v % |
| Polyvinylpyrrolidone | 0.05 w/v % |
| Benzyl alcohol | 0.5 w/v % |
| Glycerol | 2.2 w/v % |

Preparation Example 6

FLM-containing eye drops of the present invention were prepared in the same manner as that of the emulsion preparation method of Preparation Example 1 except that α-tocopherol acetate was not used, oleic acid was dissolved in the phospholipid solution by stirring, Metolose (registered trademark) SM-25 (Shin-Etsu Chemical Co., Ltd.) was used as methylcellulose, polyvinylpyrrolidone was replaced with sodium polyacrylate (degree of polymerization: 22,000 to 70,000, high viscosity; Wako Pure Chemical Industries, Co., Ltd.), potassium sorbate was replaced with phenethyl alcohol and glycerol was replaced with propylene glycol. The product was packed in the same manner as that of Preparation Example 1. The formulation was as follows:

Preparation 6

| Component | Amount and concentration |
|---|---|
| FLM | 0.02 w/v % |
| EPC | 0.98 w/v % |
| PYL | 0.42 w/v % |
| Oleic acid | 0.07 w/v % |
| Liquid paraffin No. 260-S | 7.0 w/v % |
| Metolose (registered trademark) SM-25 | 0.1 w/v % |
| Disodium EDTA | 0.01 w/v % |
| Sodium polyacrylate | 0.05 w/v % |
| Phenethyl alcohol | 0.4 w/v % |
| Propylene glycol | 2.0 w/v % |

Preparation Example 7

Methylcellulose [Metolose (registered trademark) SM-400; Shin-Etsu Chemical Co., Ltd.] was dispersed in hot water (70° C. or higher) to obtain a homogeneous hot aqueous slurry, which was then cooled under stirring to obtain a solution. Propylene glycol, histidine, sodium citrate and chlorobutanol were dissolved in the solution under stirring to obtain a solution of the water-soluble components.

FLM-containing eye drops of the present invention were prepared in the same manner as that of the emulsion preparation method of Preparation Example 1 except that α-tocopherol acetate was not used and the solution of water-soluble components described above was used in place of the solution used in Preparation Example 1. The product was packed in the same manner as that of Preparation Example 1. The formulation was as follows:

Preparation 7

| Component | Amount and concentration |
|---|---|
| FLM | 0.02 w/v % |
| EPC | 0.98 w/v % |
| PYL | 0.42 w/v % |
| Liquid paraffin No. 260-S | 7.0 w/v % |
| Metolose (registered trademark) SM-400 | 0.1 w/v % |
| Sodium citrate | 0.075 w/v % |
| Histidine | 0.02 w/v % |
| Chlorobutanol | 0.25 w/v % |
| Propylene glycol | 2.0 w/v % |

Preparation Example 8

FLM-containing eye drops of the present invention were prepared in the same manner as that of the emulsion preparation method of Preparation Example 1 except that α-tocopherol acetate was not used, cholesterol was further dissolved in the phospholipid solution under stirring, polyvinylpyrrolidone was replaced with dextran (Dextran T70; Pharmacia Fine chemicals), potassium sorbate was replaced with chlorohexidine gluconate and glycerol was replaced with sorbitol. The product was packed in the same manner as that of Preparation Example 1. The formulation was as follows:

Preparation 8

| Component | Amount and concentration |
|---|---|
| FLM | 0.02 w/v % |
| EPC | 0.98 w/v % |
| PYL | 0.42 w/v % |
| Cholesterol | 0.1 w/v % |
| Liquid paraffin No. 260-S | 7.0 w/v % |
| Metolose (registered trademark) SM-400 | 0.1 w/v % |
| Disodium EDTA | 0.01 w/v % |
| Dextran T70 | 0.05 w/v % |
| Chlorohexidine gluconate | 0.05 w/v % |
| Sorbitol | 5.0 w/v % |

Preparation Example 9

Methylcellulose [Metolose (registered trademark) SM-400; Shin-Etsu Chemical Co., Ltd.] was dispersed in hot water (70° C. or higher) to obtain a homogeneous hot aqueous slurry, which was then cooled under stirring to obtain a solution. Methyl p-hydroxybenzoate, propyl p-hydroxybenzoate, a sucrose oleic acid ester (Ryoto Sugar ester O-1570; Mitsubishi Chemical Co. Ltd.), EDTA disodium salt and glycerol were dissolved in the solution under stirring to obtain a solution of the water-soluble components.

FLM-containing eye drops of the present invention were prepared in the same manner as that of the emulsion preparation method of Example 1 except that a-tocopherol acetate was not used, palmitic acid was further dissolved in the phospholipid solution by stirring, and a solution of the water-soluble components was replaced for the above-described solution. The product was packed in the same manner as that of Preparation Example 1. The formulation was as follows:

Preparation 9

| Component | Amount and concentration |
|---|---|
| FLM | 0.02 w/v % |
| EPC | 0.98 w/v % |
| PYL | 0.42 w/v % |
| Palmitic acid | 0.14 w/v % |
| Liquid paraffin No. 260-S | 7.0 w/v % |
| Metolose (registered trademark) SM-400 | 0.1 w/v % |
| Disodium EDTA | 0.01 w/v % |
| Ryoto Sugar Ester O-1570 | 0.05 w/v % |
| Methyl p-hydroxybenzoate | 0.026 w/v % |
| Propyl p-hydroxybenzoate | 0.014 w/v % |
| Glycerol | 2.2 w/v % |

Preparation Example 10

FLM-containing eye drops of the present invention were prepared in the same manner as that of the emulsion preparation method of Example 1 except that α-tocopherol acetate was not used, liquid paraffin No. 70-S (Sanko Chemical Industry Co. Ltd.) was used as oil, polyvinylpyrrolidone was replaced with sodium polyacrylate (degree of polymerization: 22,000 to 70,000, high viscosity; Wako Pure Chemical Industries, Co., Ltd.) and potassium sorbate was replaced with thimerosal. The product was packed in the same manner as that of Preparation Example 1. The formulation was as follows:

Preparation 10

| Component | Amount and concentration |
|---|---|
| FLM | 0.02 w/v % |
| EPC | 0.98 w/v % |
| PYL | 0.42 w/v % |
| Light liquid paraffin No. 70-S | 7.0 w/v % |
| Metolose (registered trademark) SM-400 | 0.1 w/v % |
| Disodium EDTA | 0.01 w/v % |
| Sodium polyacrylate | 0.05 w/v % |
| Thimerosal | 0.01 w/v % |
| Glycerol | 2.2 w/v % |

Preparation Example 11

FLM-containing eye drops of the present invention were prepared in the same manner as that of the emulsion preparation method of Example 1 except that α-tocopherol acetate was not used, light liquid paraffin No. 200-S (Sanko Chemical Industry Co. Ltd.) was used as oil, Metolose (registered trademark) SM-100 (Shin-Etsu Chemical Co., Ltd.) was used as methylcellulose, polyvinylpyrrolidone was replaced with sodium polyacrylate (degree of polymerization: 22,000 to 70,000, high viscosity; Wako Pure Chemical Industries, Co., Ltd.) and potassium sorbate was replaced with benzalkonium chloride. The product was packed in the same manner as that of Preparation Example 1. The formulation was as follows:

Preparation 11

| Component | Amount and concentration |
|---|---|
| FLM | 0.01 w/v % |
| EPC | 0.56 w/v % |
| PYL | 0.24 w/v % |
| Light liquid paraffin No. 200-S | 4.0 w/v % |
| Metolose (registered trademark) SM-100 | 1.0 w/v % |
| Disodium EDTA | 0.01 w/v % |
| Sodium polyacrylate | 0.05 w/v % |
| Benzalkonium chloride | 0.005 w/v % |
| Glycerol | 2.2 w/v % |

Preparation Example 12

FLM-containing eye drops of the present invention were prepared in the same manner as that of the emulsion preparation method of Example 1 except that α-tocopherol acetate was not used, light liquid paraffin No. 200-S (Sanko Chemical Industry Co. Ltd.) was used as the oil, Metolose (registered trademark) SM-100 (Shin-Etsu Chemical Co., Ltd.) was used as methylcellulose, polyvinylpyrrolidone was replaced with sodium polyacrylate (degree of polymerization: 22,000 to 70,000, high viscosity; Wako Pure Chemical Industries, Co., Ltd.) and potassium sorbate was replaced with hydroxyquinoline sulfate. The product was packed in the same manner as that of Preparation Example 1. The formulation was as follows:

Preparation 12

| Component | Amount and concentration |
|---|---|
| FLM | 0.01 w/v % |
| EPC | 0.56 w/v % |
| PYL | 0.24 w/v % |
| Light liquid paraffin No. 200-S | 4.0 w/v % |
| Metolose (registered trademark) SM-100 | 0.5 w/v % |
| Disodium EDTA | 0.01 w/v % |
| Sodium polyacrylate | 0.02 w/v % |
| Hydroxyquinoline sulfate | 0.01 w/v % |
| Glycerol | 2.2 w/v % |

Preparation Example 13

FLM-containing eye drops of the present invention were prepared in the same manner as that of the emulsion preparation method of Example 1 except that α-tocopherol acetate was not used, light liquid paraffin No. 200-S (Sanko Chemical Industry Co. Ltd.) was used as oil and Metolose (registered trademark) SM-100 (Shin-Etsu Chemical Co., Ltd.) was used as methylcellulose. The product was packed in the same manner as that of Preparation Example 1. The formulation was as follows:

Preparation 13

| Component | Amount and concentration |
|---|---|
| FLM | 0.05 w/v % |
| EPC | 2.8 w/v % |
| PYL | 1.2 w/v % |
| Light liquid paraffin No. 200-S | 16.0 w/v % |

Preparation Example 14

FLM-containing eye drops of the present invention were prepared in the same manner as that of the emulsion preparation method of Example 1 except that α-tocopherol acetate and polyvinylpyrrolidone were not used, liquid paraffin No. 200-S (Sanko Chemical Industry Co. Ltd.) was used as the oil and Metolose (registered trademark) SM-100 (Shin-Etsu Chemical Co., Ltd.) was used as methylcellulose. The product was packed in the same manner as that of Preparation Example 1. The formulation was as follows:

Preparation 14

| Component | Amount and concentration |
| --- | --- |
| FLM | 0.1 w/v % |
| EPC | 6.3 w/v % |
| PYL | 2.7 w/v % |
| Liquid paraffin No. 200-S | 25.0 w/v % |
| Metolose (registered trademark) SM-100 | 0.5 w/v % |
| Disodium EDTA | 0.008 w/v % |
| Potassium sorbate | 0.1 w/v % |
| Glycerol | 2.0 w/v % |

Preparation Example 15

CB-containing eye drops of the present invention were prepared in the same manner as that of Preparation Example 1 except that CB was replaced for FLM. The product was packed in the same manner as that of Preparation Example 1. The formulation was as follows:

Preparation 15

| Component | Amount and concentration |
| --- | --- |
| CB | 0.02 w/v % |
| EPC | 0.28 w/v % |
| PYL | 0.12 w/v % |
| α-Tocopherol acetate | 0.016 w/v % |
| Liquid paraffin No. 260-S | 2.0 w/v % |
| Metolose (registered trademark) SM-400 | 0.1 w/v % |
| Disodium EDTA | 0.01 w/v % |
| Polyvinylpyrrolidone | 0.05 w/v % |
| Potassium sorbate | 0.1 w/v % |
| Glycerol | 2.2 w/v % |
| 1N NaOH | suitable amount |

Preparation Example 16

CB-containing eye drops of the present invention were prepared in the same manner as that of Preparation Example 3 except that CB was replaced for FLM. The product was packed in the same manner as that of Preparation Example 1. The formulation was as follows:

Preparation 16

| Component | Amount and concentration |
| --- | --- |
| CB | 0.02 w/v % |
| EPC | 0.21 w/v % |
| Coatsome (registered trademark) MC-6060 | 0.03 w/v % |
| PYL | 0.09 w/v % |
| Liquid paraffin No. 350-S | 13.5 w/v % |
| Metolose (registered trademark) SM-400 | 0.1 w/v % |
| Disodium EDTA | 0.01 w/v % |
| Gelatin | 0.05 w/v % |
| Potassium sorbate | 0.1 w/v % |
| Glycerol | 2.2 w/v % |

Preparation Example 17

CB-containing eye drops of the present invention were prepared in the same manner as that of Preparation Example 5 except that CB was replaced for FLM. The product was packed in the same manner as that of Preparation Example 1. The formulation was as follows:

Preparation 17

| Component | Amount and concentration |
| --- | --- |
| CB | 0.02 w/v % |
| EPC | 0.7 w/v % |
| Egg yolk lecithin LPL-20 | 0.1 w/v % |
| PYL | 0.3 w/v % |
| Liquid paraffin No. 260-S | 1.0 w/v % |
| Metolose (registered trademark) SM-1500 | 0.1 w/v % |
| Disodium EDTA | 0.01 w/v % |
| Polyvinylpyrrolidone | 0.05 w/v % |
| Benzyl alcohol | 0.5 w/v % |
| Glycerol | 2.2 w/v % |

Preparation Example 18

CB-containing eye drops of the present invention were prepared in the same manner as that of Preparation Example 10 except that CB was replaced for FLM. The product was packed in the same manner as that of Preparation Example 1. The formulation was as follows:

Preparation 18

| Component | Amount and concentration |
| --- | --- |
| CB | 0.02 w/v % |
| EPC | 0.21 w/v % |
| PYL | 0.09 w/v % |
| Light liquid paraffin No. 70-S | 13.5 w/v % |
| Metolose (registered trademark) SM-400 | 0.1 w/v % |
| Disodium EDTA | 0.01 w/v % |
| Sodium polyacrylate | 0.05 w/v % |
| Thimerosal | 0.01 w/v % |
| Glycerol | 2.2 w/v % |

Preparation Example 19

CB-containing eye drops of the present invention were prepared in the same manner as that of Preparation Example

---

-continued

| Component | Amount and concentration |
| --- | --- |
| Metolose (registered trademark) SM-100 | 0.1 w/v % |
| Disodium EDTA | 0.01 w/v % |
| Polyvinylpyrrolidone | 0.02 w/v % |
| Potassium sorbate | 0.1 w/v % |
| Glycerol | 2.0 w/v % |

1 except that CB was replaced for FLM. The product was packed in the same manner as that of Preparation Example 1. The formulation was as follows: Preparation 19

| Component | Amount and concentration |
| --- | --- |
| CB | 0.002 w/v % |
| EPC | 0.07 w/v % |
| PYL | 0.03 w/v % |
| α-Tocopherol acetate | 0.004 w/v % |
| Liquid paraffin No. 260-S | 0.1 w/v % |
| Metolose (registered trademark) SM-400 | 0.1 w/v % |
| Disodium EDTA | 0.01 w/v % |
| Polyvinylpyrrolidone | 0.05 w/v % |
| Potassium sorbate | 0.1 w/v % |
| Glycerol | 2.2 w/v % |
| 1N NaOH | suitable amount |

Preparation Example 20

CB-containing eye drops of the present invention were prepared in the same manner as that of Preparation Example 3 except that CB was replaced for FLM. The product was packed in the same manner as that of Preparation Example 1. The formulation was as follows:
Preparation 20

| Component | Amount and concentration |
| --- | --- |
| CB | 0.05 w/v % |
| EPC | 0.7 w/v % |
| Coatsome (registered trademark) MC-6060 | 0.1 w/v % |
| PYL | 0.3 w/v % |
| Liquid paraffin No. 350-S | 15.0 w/v % |
| Metolose (registered trademark) SM-400 | 0.1 w/v % |
| Disodium EDTA | 0.01 w/v % |
| Gelatin | 0.05 w/v % |
| Potassium sorbate | 0.1 w/v % |
| Glycerol | 2.2 w/v % |

Preparation Example 21

The FLM-containing emulsion of the present invention produced in Preparation Example 13 was fed into a quantitative nasal aerosol and heat-sterilized by the intermittent sterilization method to obtain nasal drops.

Preparation Example 22

FLM-containing emulsion of the present invention produced in Preparation Example 13 was fed into a dropping bottle and heat-sterilized by the intermittent sterilization method to obtain ear drops.

Preparation Example 23

The FLM-containing emulsion of the present invention produced in Preparation Example 13 was heat-sterilized by the intermittent sterilization method and then fed into an electric nebulizer to obtain an inhalation.

Preparation Example 24

The FLM-containing emulsion of the present invention produced in Preparation Example 13 was heat-sterilized by the intermittent sterilization method and then fed into an atomizer to obtain an aerosol.

Preparation Example 25

The FLM-containing emulsion of the present invention produced in Preparation Example 13 was fed into an ampoule, and the ampoule was sealed. After the heat-sterilization by the intermittent sterilization method, a liquid for internal use was obtained.

Preparation Example 26

EPC and PYL were dissolved in a mixture of hexane/ethanol [10/1 (v/v)] under stirring. Separately, FLM was dissolved in ethanol, and the obtained solution was mixed with the phospholipid solution, obtained as described above, under stirring. The solvent was evaporated with an evaporator and then with a vacuum pump to form a thin phospholipid membrane containing FLM.

Methylcellulose [Metolose (registered trademark) SM-100; Shin-Etsu Chemical Co., Ltd.] was dispersed in hot water (water for injection, 70° C. or higher) to obtain a homogeneous hot aqueous slurry, which was then cooled under stirring to obtain a solution. Glycerol and sodium citrate were dissolved in the solution under stirring to obtain a solution of these water-soluble components.

The obtained solution of the water-soluble components and liquid paraffin (No. 260-S; Sanko Chemical Industry Co. Ltd.) were added to the thin phospholipid membrane prepared as described above, and they were vigorously shaken to conduct the pre-emulsification. Water for injection was added to the pre-emulsified liquid to make the total amount 1 L. The obtained mixture was emulsified by passing through a microfluidizer (M-110EH; Microfluidics Co.) 30 times under a pressure of 740 kg/cm$^2$. After the completion of the emulsification, 1 N NaOH was added to the emulsion to adjust pH thereof to 7.4. The emulsion was filtered through a membrane having a pore diameter of 0.45 μm to obtain an FLM emulsion of the present invention containing the above-described additives. The emulsion was fed into an ampoule, which was then sealed. The emulsion in the ampoule was sterilized by heating by the intermittent sterilization method to obtain the FLM-containing injection of the present invention. The formulation was as follows:

Preparation 26

| Component | Amount and concentration |
| --- | --- |
| FLM | 0.05 w/v % |
| EPC | 2.8 w/v % |
| PYL | 1.2 w/v % |
| Liquid paraffin No. 200-S | 16.0 w/v % |
| Metolose (registered trademark) SM-100 | 0.1 w/v % |
| Sodium citrate | 0.01 w/v % |
| Glycerol | 2.0 w/v % |
| 1N NaOH | suitable amount |

Preparation Example 27

The CB-containing emulsion of the present invention produced in Preparation Example 20 was fed into a quantitative nasal aerosol and heat-sterilized by the intermittent sterilization method to obtain nasal drops.

Preparation Example 28

The CB-containing emulsion of the present invention produced in Preparation Example 20 was fed into a dropping bottle and heat-sterilized by the intermittent sterilization method to obtain ear drops.

Preparation Example 29

The CB-containing emulsion of the present invention produced in Preparation Example 20 was heat-sterilized by the intermittent sterilization method and then fed into an electric nebulizer to obtain an inhalation.

Preparation Example 30

The CB-containing emulsion of the present invention produced in Preparation Example 20 was heat-sterilized by the intermittent sterilization method and then fed into an atomizer to obtain an aerosol.

Preparation Example 31

The CB-containing emulsion of the present invention produced in Preparation Example 20 was fed into an ampoule, and the ampoule was sealed. After the heat-sterilization by the intermittent sterilization method, a drug for internal use was obtained.

Preparation Example 32

A CB emulsion of the present invention was prepared in the same manner as that of Example 26. The emulsion was fed into an ampoule. After the heat-sterilization by the intermittent sterilization method, a CB-containing injection of the present invention was obtained. The formulation was as follows:

Preparation 32

| Component | Amount and concentration |
|---|---|
| CB | 0.05 w/v % |
| EPC | 0.7 w/v % |
| PYL | 0.3 w/v % |
| Liquid paraffin No. 200-S | 15.0 w/v % |
| Metolose (registered trademark) SM-100 | 0.1 w/v % |
| Sodium citrate | 0.01 w/v % |
| Glycerol | 2.2 w/v % |

Industrial Applicability

The O/W emulsion composition of the present invention has advantages that fluorometholone or clobetasone butyrate contained therein is highly soluble in body fluids such as blood and lachrymal fluid and that the solubility and concentration of fluorometholone or clobetasone butyrate contained in the composition are excellent. Thus, in the treatment of various inflammatory diseases by the generalized or local administration of fluorometholone or clobetasone butyrate, the bioavailability of such an active ingredient can be improved and a high anti-inflammatory activity is expected. In the ophthalmic field, an anti-inflammatory activity equal or higher than that of a commercially available aqueous fluorometholone suspension or also a commercially available aqueous clobetasone butyrate suspension is expectable when it is administered in a dose smaller than that of such a suspension. Further, apprehension of systemic side effects of fluorometholone or clobetasone butyrate administered to the eyes can be relieved. Thus, the preparation excellent in the economization and storability can be provided by the present invention.

What is claimed is:

1. An O/W emulsion composition, comprising the following components A to E:
   A) fluorometholone or clobetasone butyrate,
   B) a phospholipid,
   C) an oil,
   D) a nonionic water-soluble cellulose compound, and
   E) a suitable amount of water.

2. The O/W emulsion composition of claim 1, wherein D is selected from the group consisting of methylcellulose, hydroxypropylmethylcellulose, and a mixture thereof.

3. The O/W emulsion composition of claim 1, wherein C is liquid paraffin.

4. The O/W emulsion composition of claim 1, wherein D is selected from the group consisting of methylcellulose, hydroxypropylmethylcellulose, and a mixture thereof; and C is liquid paraffin.

5. The O/W emulsion composition of claim 1, which comprises D in an amount ranging from 0.0005 to 5 w/v %.

6. The O/W emulsion composition of claim 1, which further comprises at least one member selected from the group consisting of isotonicity agents, buffering agents, thickening agents, pH adjusting agents, antioxidants, and preservatives.

7. An O/W emulsion composition, comprising the following components A to F:
   A) fluorometholone or clobetasone butyrate,
   B) a phospholipid,
   C) an oil,
   D) a nonionic water-soluble cellulose compound,
   E) a suitable amount of water, and
   F) a member selected from the group consisting of chelating agents, polycarboxylic acid compounds, and pharmaceutically acceptable salts thereof.

8. The O/W emulsion composition of claim 7, wherein D is selected from the group consisting of methylcellulose, hydroxypropylmethylcellulose, and a mixture thereof.

9. The O/W emulsion composition of claim 7, wherein C is liquid paraffin.

10. The O/W emulsion composition of claim 7, wherein D is selected from the group consisting of methylcellulose, hydroxypropylmethylcellulose and a mixture thereof, and C is liquid paraffin.

11. The O/W emulsion composition of claim 7, which comprises D in an amount ranging from 0.0005 to 5 w/v %.

12. The O/W emulsion composition of claim 7, wherein F is selected from the group consisting of ethylenediaminetetraacetic acid, citric acid, and pharmaceutically acceptable salts thereof.

13. The O/W emulsion composition of claim 7, which comprises F in an amount ranging from 0.0001 to 0.2 w/v %.

14. The O/W emulsion composition of claim 7, which further contains at least one member selected from the group consisting of isotonicity agents, buffering agents, thickening agents, pH adjusting agents, antioxidants, and preservatives.

15. A method for increasing the bioavailability of fluorometholone or clobetasone butyrate in a patient, which comprises providing an O/W emulsion composition comprising the following components A to E:
   A) fluorometholone or clobetasone butyrate,
   B) a phospholipid,
   C) an oil,
   D) a nonionic water-soluble cellulose compound, and
   E) a suitable amount of water, and administering said O/W emulsion composition to said patient.

16. The method of claim 15, wherein D is selected from the group consisting of methylcellulose, hydroxypropylmethylcellulose, and a mixture thereof.

17. The method of claim 15, wherein D is selected from the group consisting of methylcellulose, hydroxypropylmethylcellulose, and a mixture thereo; and C is liquid paraffin.

18. The method of claim 15, wherein the composition further comprises:
F) a member selected from the group consisting of ethylenediamine-tetraacetic acid, citric acid and pharmaceutically acceptable salts thereof.

* * * * *

UNITED STATES PATENT AND TRADEMARK OFFICE
CERTIFICATE OF CORRECTION

PATENT NO.    : 6,432,439 B1                                              Page 1 of 1
DATED         : August 13, 2002
INVENTOR(S)   : Suzuki et al.

It is certified that error appears in the above-identified patent and that said Letters Patent is hereby corrected as shown below:

Title page,
Item [63], Related U.S. Application Data as follows:
-- [63]        Related U.S. Application Data
        Continuation of application No. PCT/JP98/04442 filed on October 1, 1998 --

Column 1,
Line 2, insert -- This application is a continuation of application No. PCT/JP98/04442, filed October 1, 1998. --

Signed and Sealed this

Fifth Day of August, 2003

JAMES E. ROGAN
*Director of the United States Patent and Trademark Office*